United States Patent [19]
Rafal et al.

[11] Patent Number: 5,610,673
[45] Date of Patent: Mar. 11, 1997

[54] PUPIL DETECTION SYSTEM

[75] Inventors: Marc D. Rafal; Eric Starin, both of Rockville; Jeff L. Krichmar, Kensington, all of Md.

[73] Assignee: Pulse Medical Instruments, Inc., Rockville, Md.

[21] Appl. No.: 527,889

[22] Filed: Sep. 14, 1995

[51] Int. Cl.$^6$ ................................ A61B 3/14; A61B 3/10
[52] U.S. Cl. ........................... 351/210; 351/209; 351/221
[58] Field of Search .................................... 351/209, 210, 351/208, 221, 246, 205, 200

[56] References Cited

U.S. PATENT DOCUMENTS 5,410,376  4/1995  Cornsweet et al. ..................... 351/210
5,422,690  6/1995  Rothberg et al. ........................ 351/209

*Primary Examiner*—Hung Dang
*Attorney, Agent, or Firm*—Whitham, Curtis, Whitham & McGinn

[57] ABSTRACT

A pupil detection system projects two small infrared (IR) spots separated by approximately 0.5 mm. Each spot is turned on at different times (or alternatively, they can be modulated at different frequencies). The error signal produced by each spot is compared. If the errors are similar, a pupil is present. If the errors are different, no pupil is present (i.e., a blink or lost tracking). The sequencing of the IR spots and the reading of the detector data occur at the higher rates needed for accurate eye tracking.

14 Claims, 5 Drawing Sheets

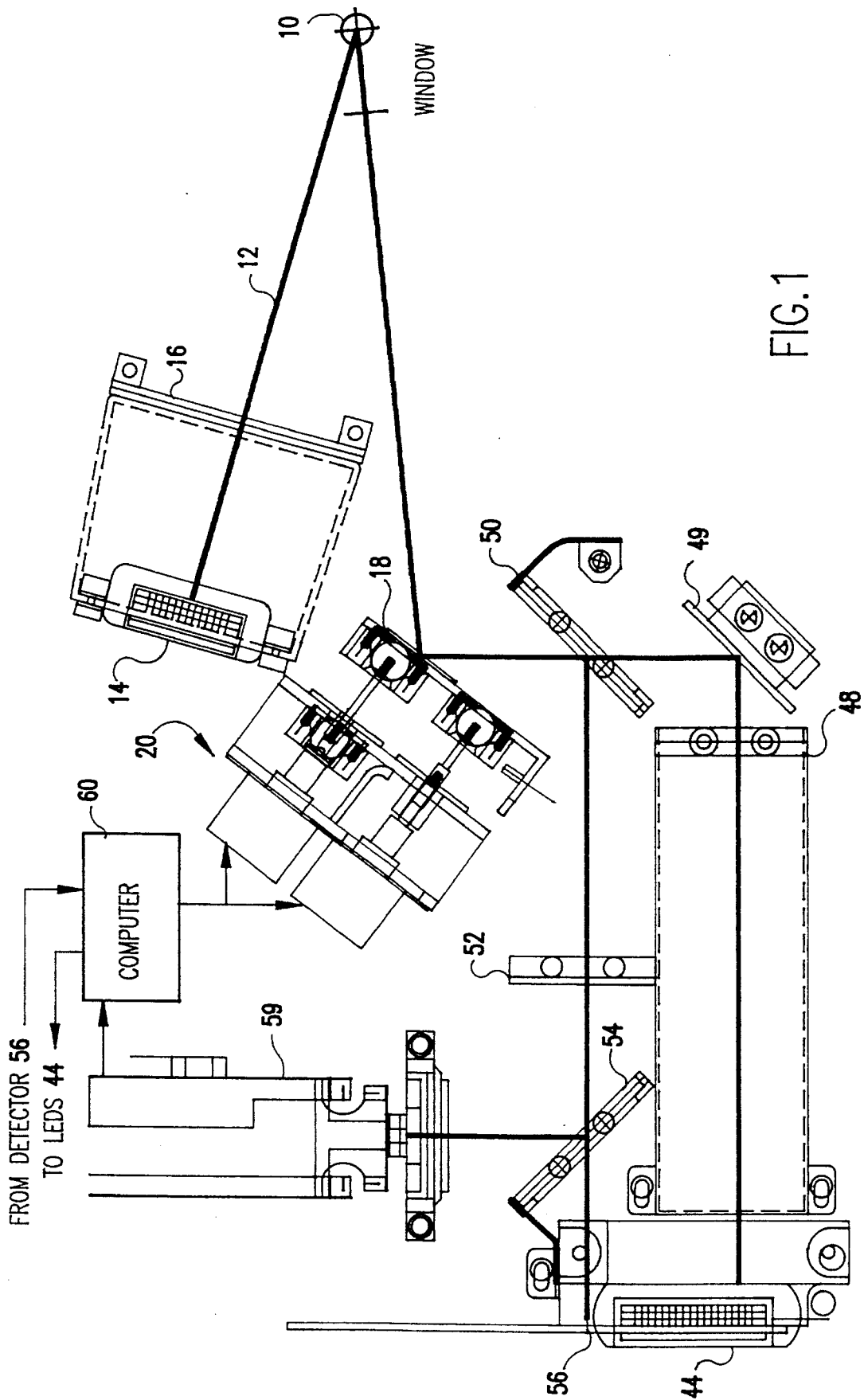

PUPIL DETECTION SYSTEM

BACKGROUND OF THE INVENTION

1. Field of the Invention

The present invention generally relates to eye tracking systems and, more particularly, to an improved pupil detection system which enhances the operation and reliability of the eye tracking system.

2. Background Description

In any eye tracking system such as the Fitness Impairment Tester disclosed in U.S. Pat. No. 5,422,690 to Tom Cornsweet, a critical capability is to determine if the signal at the detector is that of a pupil. Images other than a pupil occur prior to the start of tracking, in the event that tracking is lost or as a result of a blink. The actions taken in each of these cases is different.

In the tracking system described in U.S. Pat. No. 5,422,690, pupil recognition and blink detection are separated. Pupil recognition is based on image focus and pupil size (based on camera data) and brightness data from a quad detector. Since the focus and pupil size data were derived from a camera, a pupil detection could only be updated at the camera frame rate of 60 Hz. This low update rate limited the ability to actively search for the pupil at the beginning of a test. In addition, dependence on good focus placed significant constraints on the optics path.

While this arrangement could, in principal, detect blinks, it was not fast enough to be used to disable tracking (which operates at >600 Hz) during a blink. As a result, a blink detection scheme based solely on quad detector data was used. That scheme used the fact that the light level at the quad detector usually changed significantly during a blink. Although effective to detect most blinks, this method often detected phantom blinks. These phantom blinks occurred when, as the eye moved, the amount of light reflected by the retina changed as different retinal areas were illuminated by the incident infrared (IR) light. In these cases, tracking would often be lost since tracking was disable during these periods.

SUMMARY OF THE INVENTION

It is therefore an object of the present invention to provide an improved pupil detection system for incorporation into eye tracking systems.

According to the invention, an accurate pupil detection system is derived solely from quad detector data. In the fitness impairment tester system described in U.S. Pat. No. 5,422,690, the pupil is retro-illuminated by an IR spot that is smaller than the smallest pupil size to be measured. When a pupil is present, the resulting image at the quad detector is of a brightly lit pupil on a dark background. This image is identical wherever the IR spot lies inside the pupil, so long as all of the IR light falls into the eye. On the other hand, when the pupil is not present, the image of the reflected spot moves on the quad detector (and produces a different error signal) as the IR spot moves. The system according to the invention uses this fact by projecting two small IR spots separated by approximately 0.5 mm rather than a single IR spot. Each spot is time multiplexed (or alternatively, they can be modulated at different frequencies). The error signal produced by each spot is compared. If the errors are similar, a pupil is present. If the errors are different, no pupil is present (i.e., a blink or lost tracking). The sequencing of the IR spots and the reading of the quad detector data occur at the higher rates needed for tracking (approximately 1000 Hz).

The improved pupil detection system according to the present invention has several advantages including more accurate blink detection for improved tracking, more accurate and faster pupil detection allowing rapid initial capture and recapture if tracking is lost, and the ability to capture and track using only the quad detector data thus allowing an automated system without a camera (a high cost component) if pupil data are not required. Because there is no dependence on image focus, more reliable tracking is achieved with less critical optics.

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a schematic diagram showing the mechanical and optical components of the eye tracking and pupil imaging system;

DETAILED DESCRIPTION OF A PREFERRED EMBODIMENT OF THE INVENTION

Figure 2A:
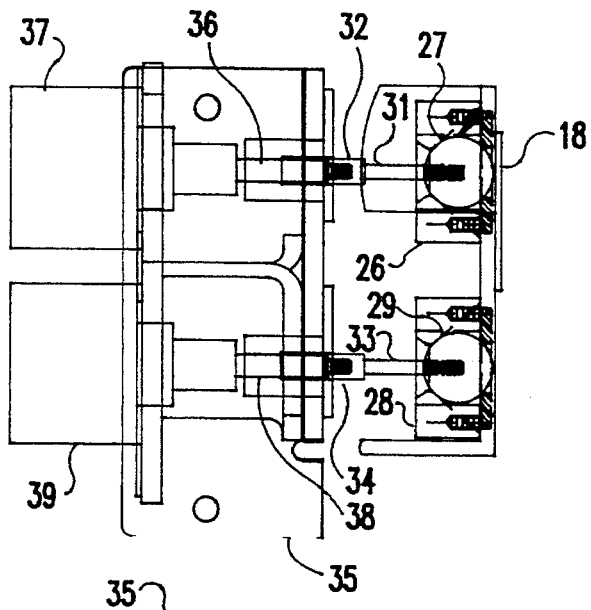
FIGS. 2A, 2B and 2C are, respectively, top, side and front views of the mirror positioning system used in the imaging system shown in FIG. 1.

Referring now to the drawings, and more particularly to FIG. 1, there is shown in schematic form the basic components of the eye tracking system incorporating the improved pupil detection system according to a preferred embodiment of the invention. The subject's eye is positioned relative to the eyepiece 10 so that initially the subject's gaze is aligned along center line 12 toward a pupil stimulus and fixation target 14. Interposed between the fixation target 14 and the eyepiece is an objective lens 16 in the form of a Fresnel lens.

Figure 2B:
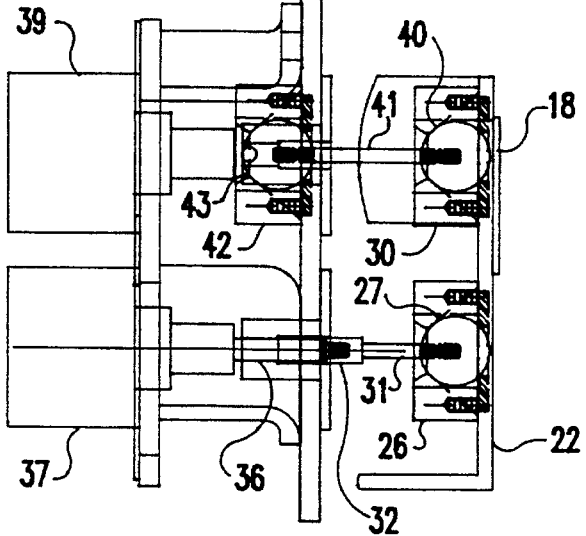
Figure 2C:
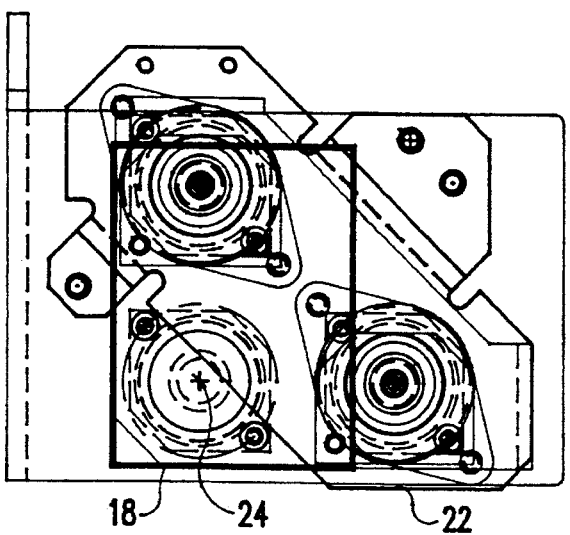

The tracking system itself includes a tracking mirror 18 which pivots about two perpendicular axes under control of a mirror positioning system 20, shown in more detail in FIGS. 2A, 2B and 2C, to which reference is now made. The tracking mirror 18 is mounted on a plate 22 having a single pivot point 24. The back of the plate 22 is fitted with three pockets, two of which, 26 and 28, are shown in FIG. 2A. The pockets 26 and 28 capture balls 27 and 29, respectively. The third pocket 30, shown in FIG. 2B, is located at the pivot point 24. This third pocket receives a third ball and is described in more detail below. The balls 27 and 29 are drilled and tapped to receive respective threaded rods 31 and 33 which are, in turn, connected through bushings 32 and 34 to the shafts 36 and 38 of linear stepper motors 37 and 39 mounted to a base plate 35.

Referring again to FIG. 2B, the third ball 40 received in pocket 30 is also drilled and tapped to receive a threaded rod 41. This rod 41 is threaded into a fourth ball 42 which is drilled and tapped to receive the rod. A fourth pocket 43 mounted on the base plate 35 receives the fourth ball 42.

As can be seen in FIG. 2C, the ball-and-pocket mountings 26, 27 and 28, 29 are on a line that is parallel to a diagonal of the tracking mirror 18, while the ball-and-pocket mounting 30, 40 is at the pivot point 24. As a result, the mirror 18 may be freely pivoted about pivot point 24 to rotationally move about two perpendicular axes under the control of the two stepper motors 37 and 39. The third ball-and-pocket mounting 30, 40 and the fourth ball-and-pocket mounting 42, 43 coupled by the rod 41 between the balls 40 and 42 form a "dumb bell" linkage that allows the pivot point 24 to move slightly to prevent binding of the shafts of the stepper motors, which would occur if the pivot were rigid.

Figure 3A:
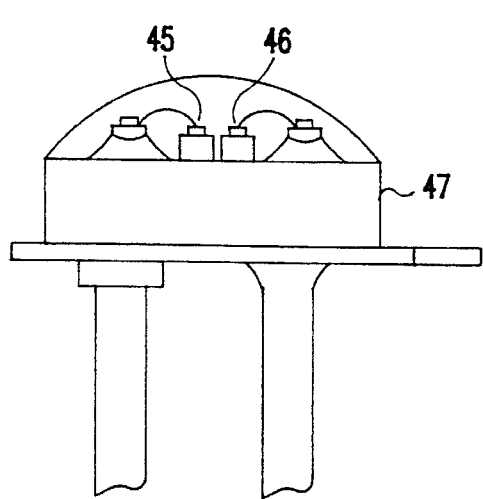
FIGS. 3A and 3B are, respectively, a side view and a top view showing the LEDs in a common header.
Figure 3B:
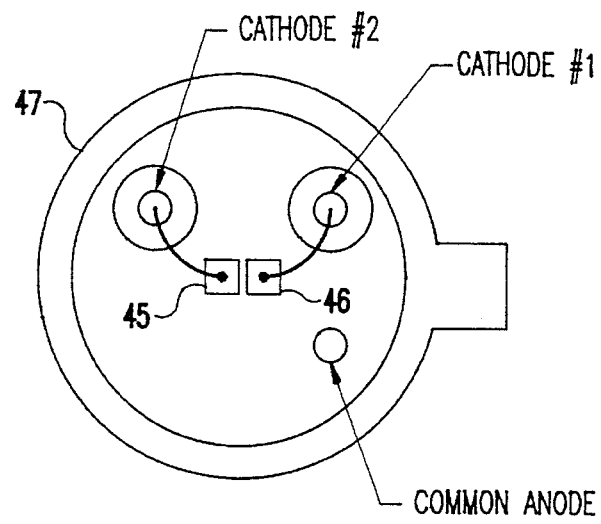

Returning now to FIG. 1, the pupil of the subject's eye is illuminated by a dual source infrared (IR) light emitting diode (LED) 40. The dual source LED 44 is used to project two spatially separated spots at the subject's pupil. As shown in FIGS. 3A and 3B, the dual source LED is constructed by placing two LED chips 45 and 46 side by side on a header 47 with appropriate bond wires and leads to allow each chip to be individually energized. The separation of the chips, in combination with the magnification of the optics of the tracking system, provides the appropriate separation of the sources at the plane of the subject's pupil.

The light from dual source LED 44 passes through lens 48 and is reflected by fixed mirror 49, and from there passes through a beam splitter 50 to be reflected by the tracking mirror 18 to the subject's pupil, where it forms an image of the dual IR spots that is much smaller than the smallest that the pupil ever gets. The light thus passes through the pupil and falls on the retina, where it is back scattered.

Figure 4:
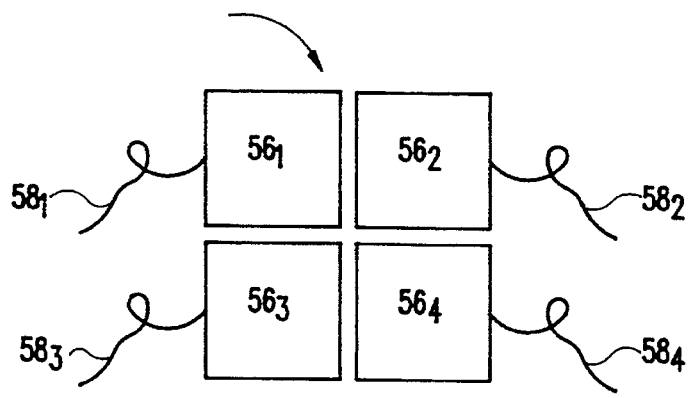
FIG. 4 is a plan view showing the arrangement of the quadrant detector used in the system of FIG. 1.

Back scattered light that exits the subject's eye through the pupil is reflected by the mirror 18 to beam splitter 50 which reflects the light through imaging lens 52 and beam splitter 54 to a quadrant detector 56, shown in more detail in FIG. 4. The quadrant detector 56, as shown in FIG. 4, comprises IR detectors $56_1$, $56_2$, $56_3$, and $56_4$, one for each of first, second, third, and fourth quadrants of an image plane onto which an image of the subject's pupil is projected by the beam splitter 50. Wires $58_1$, $58_2$, $58_3$, and $58_4$, respectively connected to IR detectors $56_1$ $56_2$, $56_3$, and $56_4$, carry analog signals corresponding to the amount of IR light falling on the corresponding detector. These analog signals are combined and digitized for processing by a computer (shown in FIG. 1).

Returning again to FIG. 1, if the pupil is approximately aligned, light from the dual IR LED source 44 enters the pupil about at its center and illuminates the retina. Light back scattered from the retina that emerges from the pupil is reflected by the tracking mirror 18 and the beam splitter 50 and is split by beam splitter 54. Half of the light passing through beam splitter 54 forms an image of the pupil approximately centered on the silicon quadrant photo detector 56. The other half of the light falling on beam splitter 54 is reflected to a charge coupled device (CCD) camera 59. In some applications, the beam splitter 54 and the camera 59 are optional. The outputs from the quadrant photo detector 56 and, if used, the CCD camera 59 are input to computer 60. The computer 60 is of conventional design employing a microprocessor and supporting hardware and software to digitize the analog signals from the quadrant photo detector 56 and to sample the output of the CCD camera 59. The outputs of the computer 60 are control signals to the dual LED 44, tracking controls to the stepper motors 37 and 39, and a user display (not shown), such as in the current fitness impairment tester described in U.S. Pat. No. 5,422,690.

The current fitness impairment tester described in U.S. Pat. No. 5,422,690 uses two logical flags that determine when to initiate and pause tracking. These are Pupil_Present and Blinking. Before initiating tracking at the beginning of the test, the Pupil_Present flag indicates when a pupil is in the detector's field of view. Once tracking begins, the Blinking flag indicates that a blink has occurred, during which tracking is paused since the error signal is no longer valid.

The Pupil_Present flag is based on the following differences between pupil and no pupil conditions:

|  | No Pupil | Pupil |
| --- | --- | --- |
| IR Signal Level (Quad Detector) | Low | High |
| Pupil Diameter | <1 mm | >1 mm |
| Focus | Out of Focus | In Focus |

Focus is determined by measuring the pupil diameter at three different threshold values. There are several limitations to the above techniques that motivate an improved system. First, the separation between the No Pupil and Pupil conditions is not large in some individuals. This allows the Pupil_Present flag to be incorrect under certain conditions leading to the start of tracking before a pupil is present or a loss of tracking. Second, the determination of Pupil_Present is based on camera measurement which only occur at 16 ms intervals while tracking occurs at 1 ms intervals.

Since tracking must be paused during a blink, a blink indication must be derived from the quad detector signal. The Blinking flag is based on the rapid decrease in IR signal at the quad detector when a blink occurs. The flag is cleared when a complementary increase occurs or a maximum time has elapsed. Because large changes in IR level can occur during rapid eye movements, the Blinking flag can become true incorrectly.

Figure 5A:
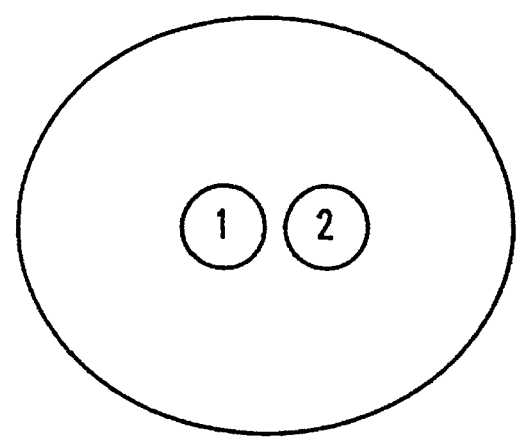
FIGS. 5A, 5B and 5C are schematic representations of the respective conditions of pupil present, pupil not present and pupil partially ;present in the practice of the invention.
Figure 5B:
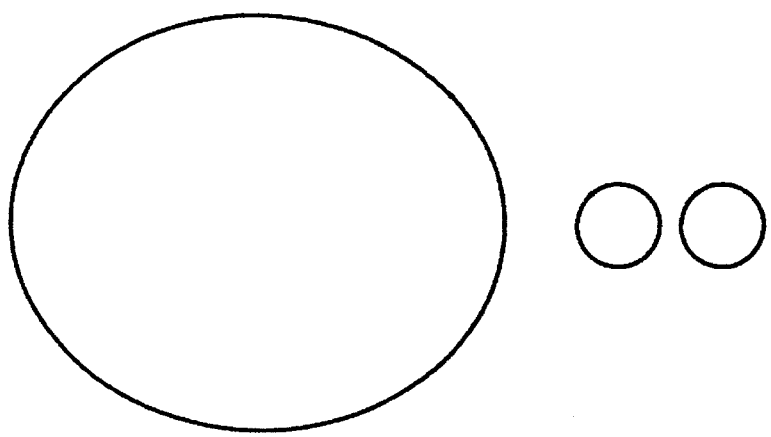
Figure 5C:
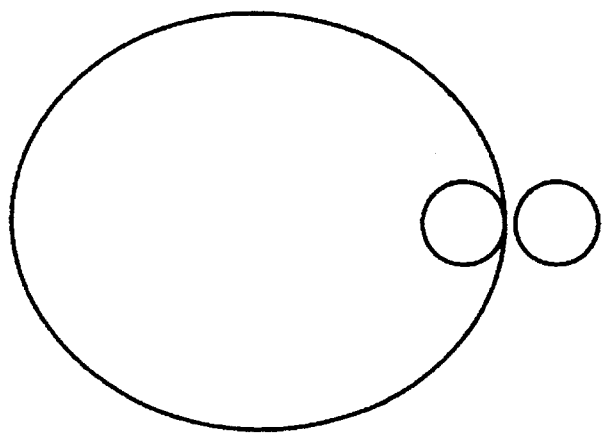

According to the present invention, the IR source of the prior system is modified to project two independent IR spots separated by, say, 0.5 ram, each spot being time multiplexed or modulated at a different frequency. This time or frequency modulation of the LED is controlled by the computer 60 and makes it possible to capture two independent quad detector error signals. When a pupil is present, both error signals will be the same since both spots will fall inside the pupil. However, if no pupil is present, the image of each spot will fall on different areas of the quad detector 56 and thus produce very different error signals. FIGS. 5A, 5B and 5C illustrate the various conditions summarized in the table below.

|  | Condition | Characteristic |
| --- | --- | --- |
| FIG. 5A | Pupil Present | E1~E2 S1~S2 |
| FIG. 5B | Pupil Not Present or Blink | E< >E2 S1~S2 |
| FIG. 5C | Pupil Partially Present | E1< >E2 S1> >S2 |

In the table, E1, E2, S1, and S2 are the horizontal error from spot 1, the horizontal error from spot 2, the sum signal from spot 1, and the sum signal from spot 2, respectively. In addition to the above requirements, S1 and S2 must also each be within a defined range to ensure that the signals are neither saturated nor dominated by noise.

Figure 6:
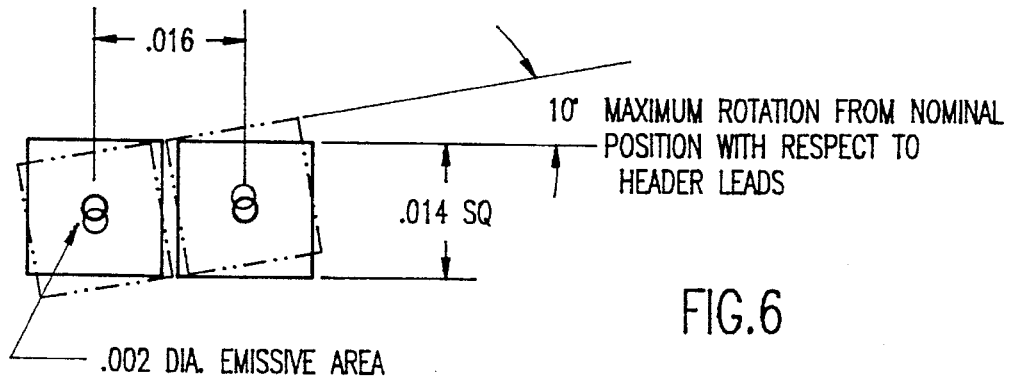
FIG. 6 is a plan view showing the critical relationships of the two light emitting diodes (LEDs) in their common header.

As may be appreciated from the illustrations in FIGS. 5A, 5B and 5C, the relative positions of the two IR sources in the dual source LED 40 are relatively critical. However, the mounting of the LED chips 42 and 44 on the common header as shown in FIGS. 3A and 3B allows for considerable precision in the relative separations of the two sources. Further, the mounting of the header itself to its printed circuit board provides precision in the angular orientation of the two sources about the axis of the header. FIG. 6 shows the maximum allowed rotation of the LED chips 42 and 44 with respect to the header leads. This is well within normal manufacturing tolerances.

In the preferred embodiment, the LEDs are time multiplexed. During each one millisecond sample period, the LEDs are sequenced as follows:

|  | LED1 | LED2 | Period Name |
|---|---|---|---|
| 0 to 64 μsec | On | Off | LED1 |
| 64 to 128 μsec | Off | Off | Dark Period |
| 128 to 192 μsec | Off | On | LED2 |
| 192 to 1000 μsec | On | On | Both |

Figure 7:
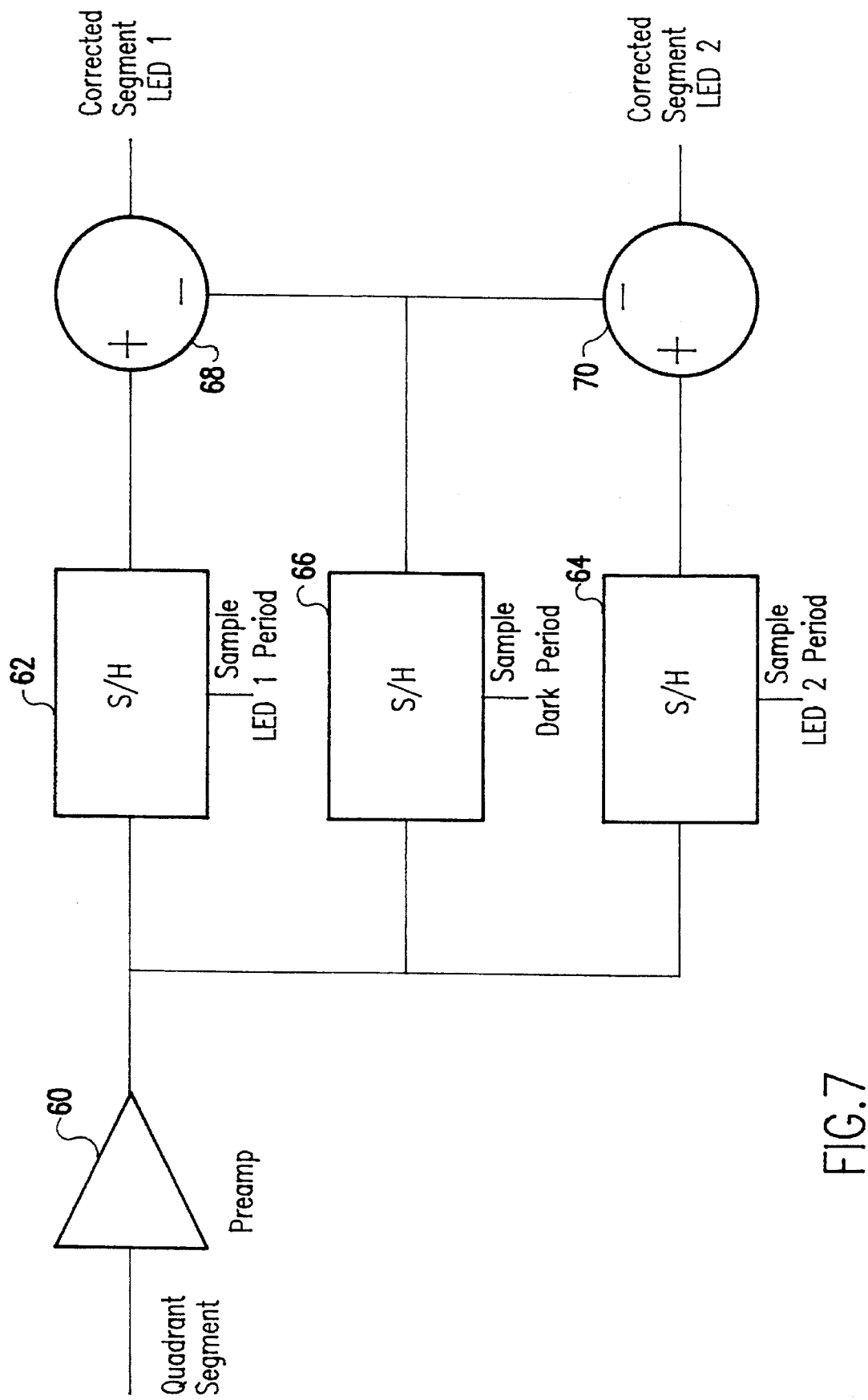
FIG. 7 is a block diagram showing the circuitry for processing each quad detector segment signal for the two LEDs.

As shown in FIG. 7, the quad signals from LED 1 and LED2 from one quad detector segment are amplified by a preamplifier are captured in sample-and-hold circuits 62 and 64 during the LED 1 and LED2 periods, respectively. A third sample of the quad signals is captured in sample-and-hold circuit 66 during the dark period. The dark period signals are subtracted from the sampled LED signals in subtractors 68 and 70 to correct for DC drift, low frequency noise, 60 Hz interference, and any ambient light that might have fallen on the quad detector 56. The corrected quad detector signals are used to form the LED1 and LED2 error signals. The period where both LED signals are turned on provides maximum IR illumination for any other sensors, for example the optional CCD camera 59. The circuit shown in FIG. 7 is repeated for each of the quad detector segments.

The error signals used in the current fitness impairment tester described in U.S. Pat. No. 5,422,690 indicate only the direction and the error and not the actual amount. The errors are given by $$X \text{ Error} = \frac{(A+D)-(B+C)}{A+B+C+D}$$

$$Y \text{ Error} = \frac{(A+B)-(C+D)}{A+B+C+D}$$

where A, B, C, and D are the signal levels from the quadrant detector starting in the upper right hand quadrant and proceeding counter clockwise. The sign of these errors will correctly indicate the direction of any position error. However, the magnitude of the error will depend on the diameter of the pupil in addition to the size of the true position error.

This is improved in the present invention when the optional CCD (charge coupled device) camera 59 is used to determine pupil diameter. The diameter information may be used in conjunction with the above error signals to compute an accurate positional error. In addition to improving tracking, this true error can be added to the motor position to obtain a corrected pupil position. In the preferred embodiment, the corrected positions are accurate to approximately one tenth the size of a motor step. This dramatically improves the analysis of position data.

An accurate positional error is obtained using the following steps:

1. Determine the direction of the X Error using the conventional means described above.
2. Determine the magnitude of the X Error as follows:

if A+D<B+C, solve using numerical methods the following equation for x $$\frac{A+D}{B+C} = \frac{\frac{\Pi}{2} r^2 - x\sqrt{r^2 - x^2} - r^2\sin^{-1}\left(\frac{x}{r}\right)}{\frac{\Pi}{2} r^2 + x\sqrt{r^2 - x^2} + r^2\sin^{-1}\left(\frac{x}{r}\right)}$$

but if A+D>B+C, solve using numerical methods the following equation for x $$\frac{B+C}{A+D} = \frac{\frac{\Pi}{2} r^2 - x\sqrt{r^2 - x^2} - r^2\sin^{-1}\left(\frac{x}{r}\right)}{\frac{\Pi}{2} r^2 + x\sqrt{r^2 - x^2} + r^2\sin^{-1}\left(\frac{x}{r}\right)}$$

where A, B, C, and D are the quadrant as described above, x is the true x-axis error, and r is the pupil radius.

3. Repeat the above procedures for the y-axis.

The primary advantages of this approach are the following:

single flag for Pupil_Present and Blink,

Pupil_Present updated at 1 ms rate (does not use camera data), thus allowing faster acquisition, larger differentiation between pupil and no pupil conditions resulting in less chance for error, eye movements do not cause Blink to be true, and improved accuracy of position measurements.

The invention exhibits fewer losses of tracking and fewer data anomalies. Because of the larger differentiation between pupil and no pupil conditions, no false tracking occurs on eye lids or the like.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. An improved pupil detection system for use in an eye tracking system comprising:

first and second spatially separated sources of infrared light;

optics forming images of said first and second sources of infrared light, said images being separated by a predetermined small distance, a combined size of said images being smaller than the smallest that a pupil of the eye ever becomes;

a tracking mirror movable about at least one axis and directing the infrared light toward the pupil of the eye, infrared light passing through the pupil of the eye and falling on the eye's retina where it is back scattered to back light the pupil, and said tracking mirror also reflecting light from the back lighted pupil;

a beam splitter intercepting the light from the back lighted pupil and reflected by said tracking mirror;

a detector positioned to receive light from said beam splitter, said detector having at least two outputs connected to provide a measure of decentering of the infrared light on said detector.

2. The improved pupil detection system recited in claim 1 further comprising:

a linear motor connected to said tracking mirror for moving said tracking mirror about said one axis; and computer means connected to receive said at least two outputs from said detector and providing an output to said linear motor for controlling movement of the tracking mirror about said one axis to track movement of a pupil.

3. The improved pupil detection system recited in claim 1 wherein the first and second spatially separated sources of infrared light comprise a pair of infrared light emitting diodes mounted on a common header.

4. The improved pupil detection system recited in claim 1 wherein the first and second spatially separated sources of infrared light are energized at different times.

5. The improved pupil detection system recited in claim 1 further comprising multiplexing means for time multiplexing the energization of the first and second spatially separated sources of infrared light.

6. The improved pupil detection system recited in claim 1 further comprising multiplexing means for frequency multiplexing the energization of the first and second spatially separated sources of infrared light.

7. The improved pupil detection system recited in claim 1 wherein the detector is a quadrant diode detector, said detector having four outputs connected to provide a measure of decentering of the infrared light on said detector.

8. The improved pupil detection system recited in claim 7 further comprising:

a second beam splitter intercepting the light from the first beam splitter, a portion of said intercepted light being passed by the second beam splitter to said detector and a portion of the intercepted light being reflected by the second beam splitter; and a charge coupled device camera receiving light reflected by said second beam splitter for measuring pupil diameter.

9. The improved pupil detection system recited in claim 8 further comprising calculating means responsive to measured pupil diameter for calculating true position errors.

10. The improved pupil detection system recited in claim 1 wherein said tracking mirror is movable about two mutually perpendicular axes, said axes defining a pivot point, and wherein the detector is a quadrant diode detector, said detector having four outputs connected to provide a measure of decentering of the infrared light on said detector.

11. The improved pupil detection system recited in claim 10 wherein said tracking mirror is mounted on a tracking assembly comprising:

first, second and third captured ball mountings attached to a first plate on which the tracking mirror is mounted, the first and second captured ball mountings being positioned along a line parallel to a diagonal of the tracking mirror and the third captured ball mounting being located at said pivot point of the tracking mirror;

first and second linear motors mounted on a second plate and connected to said first and second captured ball mountings for independently moving said first and second captured ball mountings in directions nominally perpendicular to said plate to rotate said tracking mirror about said two mutually perpendicular axes; and a fourth captured ball mounting attached to said third ball mounting and mounted on said second plate, said third and fourth captured ball mountings allowing said pivot point to move slightly and prevent binding of the shafts of the first and second linear motors.

12. The improved pupil detection system recited in claim 11 further comprising computer means connected to receive said four outputs from said detector and providing outputs to said first and second linear motors for controlling the movement of the tracking mirror about said two mutually perpendicular axes to track movement of a pupil.

13. The improved pupil detection system recited in claim 12 further comprising:

a second beam splitter intercepting the light from the first beam splitter, a portion of said intercepted light being passed by the second beam splitter to said detector and a portion of the intercepted light being reflected by the second beam splitter; and a charge coupled device camera receiving light reflected by said second beam splitter for measuring pupil diameter.

14. The improved pupil detection system recited in claim 13 wherein said computer means is responsive to measured pupil diameter for calculating true position errors.

* * * * *